United States Patent [19]

Zahn et al.

[11] Patent Number: 4,873,546
[45] Date of Patent: Oct. 10, 1989

[54] COLOR PRINTING METHOD AND APPARATUS

[75] Inventors: Wolfgang Zahn, Munich; Manfred Fürsich, Taufkirchen; Wilhelm Nitsch, Munich; Hans-Jürgen Rauh, Strasslach-Hailafing; Helmut Treiber, Munich, all of Fed. Rep. of Germany

[73] Assignee: AGFA-Gevaert Aktiengesellschaft, Leverkusen, Fed. Rep. of Germany

[21] Appl. No.: 264,399

[22] Filed: Oct. 28, 1988

[30] Foreign Application Priority Data

Nov. 6, 1987 [DE] Fed. Rep. of Germany ....... 3737775

[51] Int. Cl.$^4$ .............................................. G03B 27/73
[52] U.S. Cl. ...................................... 355/38; 355/68; 355/77
[58] Field of Search .............................. 355/38, 68, 77

[56] References Cited

U.S. PATENT DOCUMENTS

| | | | |
|---|---|---|---|
| 4,279,502 | 7/1981 | Thurm et al. | 355/38 |
| 4,406,538 | 9/1983 | Bühler | 355/38 X |
| 4,589,766 | 5/1986 | Fürsich et al. | 355/38 |

Primary Examiner—L. T. Hix
Assistant Examiner—D. Rutledge
Attorney, Agent, or Firm—Peter K. Kontler

[57] ABSTRACT

Light containing blue, green and red radiation is passed through a colored original which is to be printed on color copy material. The transmitted light is spread out into a color spectrum which extends across a first wavelength range generally corresponding to the blue portion of the spectrum, a second wavelength range generally corresponding to the green portion of the spectrum and a third wavelength range generally corresponding to the red portion of the spectrum. The intensity of the transmitted light is measured throughout the spectrum and average of the resulting raw intensities are taken oer each of a series of wavelength intervals which are much shorter than the first, second and third ranges. The copy material has a gamma value for each wavelength interval and such gamma value represents the spectral sensitivity of the copy material in the corresponding interval. The average intensity for each wavelength interval is multiplied by the respective gamma value to yield a corrected intensity. The corrected intensities for each wavelength range are summed to generate first, second and third sums corresponding to the first, second and third ranges and respectively representing the blue, green and red densities of the original. The first, second and third sums are used to calculate the respective amounts of blue, green and red light required to print the original with a neutral gray density.

30 Claims, 3 Drawing Sheets

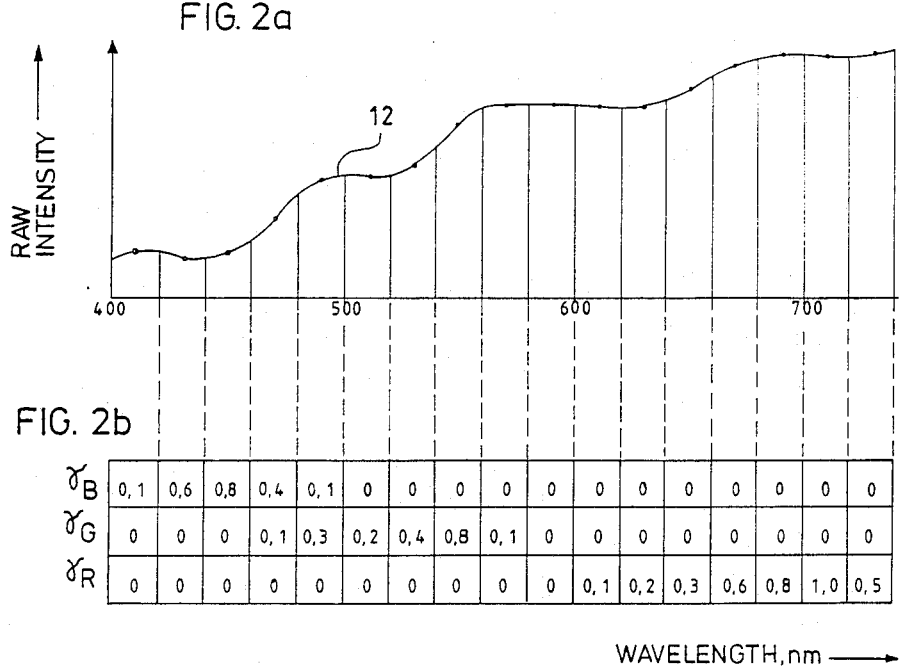
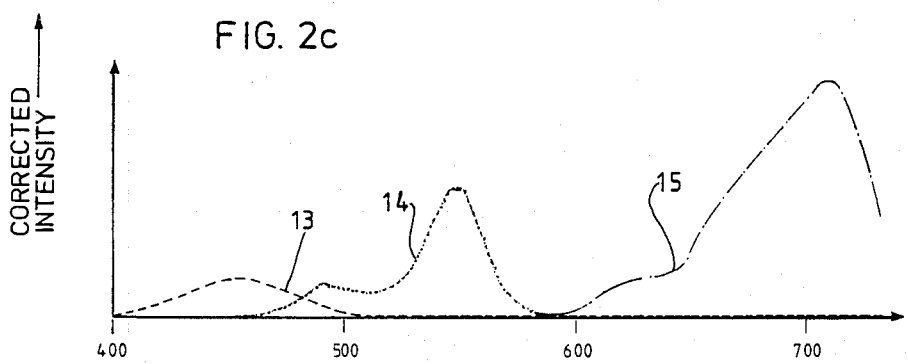

COLOR PRINTING METHOD AND APPARATUS

BACKGROUND OF THE INVENTION

The invention relates generally to color copying.

More particularly, the invention relates to a method of and an apparatus for determining the amounts of blue, green and red copy light required to reproduce a colored original on color copy material.

In order to determine the amounts of blue, green and red copy light required for reproduction of a colored original, the blue, green and red densities of the original are measured. It is generally attempted to adjust the spectral sensitivities of the density measuring system as closely as possible to the spectral sensitivities of the copy material. This is done so that the original may, during the measurement procedure, be evaluated with the "eyes" of the copy material, so to speak.

The U.S. Pat. No. 4,589,766 teaches that mixed production, i.e., the copying of different types of film, may be carried out with a single memory when measurement of the color densities of the films is performed under conditions which allow the spectral sensitivities of the copy material to be approximated as closely as possible. The spectral transmissivity curves of the color filters disposed in front of the measuring cells are here calculated step-by-step as a function of wavelength based on the existing physical magnitudes. These curves are subsequently attained by vapor depositing absorption layers of different thickness on the filter carriers. In this manner, optimal adjustment of the measuring system to the spectral sensitivities of the copy material is achieved taking into account non-uniformity in the spectral sensitivities of the measuring cells and differing spectral absorption characteristics in the measuring and copying color channels.

The preceding filter production technique is exceedingly complicated. Moreover, it is difficult to regulate with the required accuracy, especially when there are small variations in the spectral sensitivities of the copy material.

OBJECTS AND SUMMARY OF THE INVENTION

It is an object of the invention to provide a more easily regulated procedure for adjusting the spectral sensitivities of a density measuring system to the spectral sensitivities of a copy material.

Another object of the invention is to provide a procedure which allows the spectral sensitivities of a density measuring system to be more precisely adjusted to the spectral sensitivities of a copy material.

An additional object of the invention is to provide an apparatus which enables the spectral sensitivities of a density measuring system to be adjusted to the spectral sensitivities of a copy material with relative ease.

A further object of the invention is to provide an apparatus which makes it possible to adjust the spectral sensitivities of a density measuring system to the spectral sensitivities of a copy material with a relatively high degree of precision.

The preceding objects, as well as others which will become apparent as the description proceeds, are achieved by the invention.

One aspect of the invention resides in a method of copying a colored original, e.g., a negative, onto color copy material, that is, copy material sensitized to blue, green and red light. The method involves passing light having blue, green and red components through the orignal and forming a color spectrum from the light transmitted through the original. The spectrum extends across a first wavelength range corresponding to blue-containing radiation, a second wavelength range corresponding to green-containing radiation and a third wavelength range corresponding to red-containing radiation. The copy material has respective first, second and third spectral sensitivites in the first, second and third ranges and these spectral sensitivities are respectively represented by first, second and third factors. The method further involves measuring the intensity of the transmitted light in the first, second and third ranges to obtain respective first, second and third raw intensities and modifying, e.g., multiplying, the raw intensities by the first, second and third factors, respectively, to yield first, second and third corrected intensities. The amounts of blue, green and red copy light which will produce a copy of desired density on the copy material are then calculated using the corrected intensities.

Preferably, the raw intensity of the transmitted light is measured at a plurality of wavelengths in each of the ranges. Each wavelength lies in a respective segment or wavelength interval of the corresponding range and each segment may be assigned a spectral sensitivity factor for the copy material. Here, the raw intensity for each segment is modified by the respective factor to obtain a corrected intensity for the segment and the corrected intensities for each range are summed to derive first, second and third sums respectively representing blue, green and red densities of the original. Calculation of the amounts of copy light is then performed using the sums.

The steps of forming a spectrum, measuring and modifying the raw intensities and summing the corrected intensities may be performed for different regions of the original individually so that first, second and third sums are obtained for each region. The step of calculating the amounts of copy light is here effected using the first, second and third sums from all regions. The sums from the various regions may be stored prior to calculation.

The original may be conveyed along a predetermined path for density measurement and copying. In such an event, light for density measurement may be passed through the original region-by-region by covering all but a strip-like portion of a measuring location of the path. Such strip-like portion may be elongated transversely of the path.

According to another embodiment of the invention, the steps of forming a spectrum, measuring and modifying the raw intensities and summing the corrected intensities each are performed for the major part of, or the entire, original at one time. The sums for the different wavelength ranges may here be considered to represent LATD values.

In an additional embodiment of the invention, the steps of forming a spectrum, measuring and modifying the raw intensities and summing the corrected intensities each are performed for at least the major part of the original at one time and the method further comprises passing additional light having blue, green and red components through such part of the original. The transmitted additional light is treated, e.g., filtered, to partially adjust for the spectral sensitivities of the copy material and the intensities of the blue, green and red components of the transmitted additional light are measured. The resulting intensities are processed to derive first, second and third values respectively representing blue, green and red densities of the original. A first parameter is established from the first sum and first value, a second parameter from the second sum and second value and a third parameter from the third sum and third value, e.g., by forming quotients of the first sum and first value, second sum and second value, and third sum and third value. Raw amounts of blue, green and red copy light are calculated from the first, second and third values and such raw amounts are modified or corrected by means of the first, second and third parameters, respectively. The raw amounts of copy light may, for instance, be multiplied by the corresponding parameters. The first, second and third values, as well as the first, second and third sums, may be considered to represent LATD values.

Another aspect of the invention resides in an apparatus for copying a colored original onto color copy material. The apparatus, which is particularly well-suited for carrying out the method of the invention, comprises means for illuminating the original with light having blue, green and red components and means for forming a color spectrum from light transmitted through the original. The forming means may, for example, include a prism system or grating system in combination with a lens system and is effective to generate the spectrum such that the latter extends across a first wavelength range corresponding to blue-containing radiation, a second wavelength range corresponding to green-containing radiation and a third wavelength range corresponding to red-containing radiation. The apparatus further comprises means for measuring the intensity of the transmitted light in the first, second and third ranges to obtain respective first, second and third raw intensities and means for processing the raw intensities. The copy material has respective first, second and third spectral sensitivities in the first, second and third ranges and the processing means includes storage means for first, second and third factors, e.g., gamma values, respectively representing the first, second and third spectral sensitivities. The processing means additionally includes calculating means programmed to modify, e.g., multiply, the first, second and third raw intensities by the first, second and third factors, respectively, so as to obtain first, second and third corrected intensities. The calculating means is also programmed to use the corrected intensities in calculating the amounts of blue, green and red copy light which will produce a copy of desired density on the copy material.

The measuring means preferably comprises a multiplicity of light-sensitive elements including a first group for the first range, a second group for the second range and a third group for the third range. The measuring means may be designed to measure the raw intensity of the transmitted light at a plurality of wavelengths in each of the ranges and each wavelength then lies in a respective segment or wavelength interval of the corresponding range. A spectral sensitivity factor for the copy material is assigned to each segment and the calculating means is programmed to modify the raw intensity for each segment by the respective factor and to sum the resulting corrected intensities for each range. This yields first, second and third sums respectively representing blue, green and red densities of the original.

In accordance with the invention, measurement light which has passed through the original is spread out into a color spectrum in which every location is assigned to a specific wavelength interval. This allows the intensity of the measurement light to be determined interval-by-interval without taking color into account. Furthermore, a numerical factor or gamma value corresponding to each wavelength interval may be established for the copy material by appropriate evaluation of the spectral sensitivity of the latter taking into consideration the relative spectral distribution of the copy light in the copy light channel or channels. Each gamma value represents the effectiveness of copy light having wavelengths in the respective interval in darkening or coloring the copy material. Multiplication of the measured or raw intensities of the measurement light in the various wavelength intervals by the corresponding factors or gamma values thus makes it possible to precisely calculate the effective transmissivity of the original. For any copy material, all that is required for this calculation is a table listing effectiveness factors or gamma values as a function of wavelength for each of the primary colors blue, green and red. By summing the weighted intensity values, i.e., the raw intensity values of the measurement light multiplied by the gamma values for the respective wavelength intervals, corresponding to each color, it becomes possible to establish the appropriate copying or printing density for the different colors of a given portion of the original.

The novel features which are considered as characteristic of the invention are set forth in particular in the appended claims. The improved copying method, as well as the construction and mode of operation of the improved copying apparatus, together with additional features and advantages of the method and apparatus will, however, be best understood upon perusal of the following detailed description of certain specific embodiments when read in conjunction with the accompanying drawings.

BRIEF DESCRIPTION OF THE DRAWINGS

FIG. 2a is a plot of raw intensity versus wavelength for light which has travelled through a colored original to be copied;

FIG. 2b is a table listing gamma values for one type of color copy paper as a function of wavelength;

FIG. 2c is a plot of corrected intensity versus wavelength for light which has travelled through a colored original, to be copied.

DESCRIPTION OF THE PREFERRED EMBODIMENTS

Figure 1:
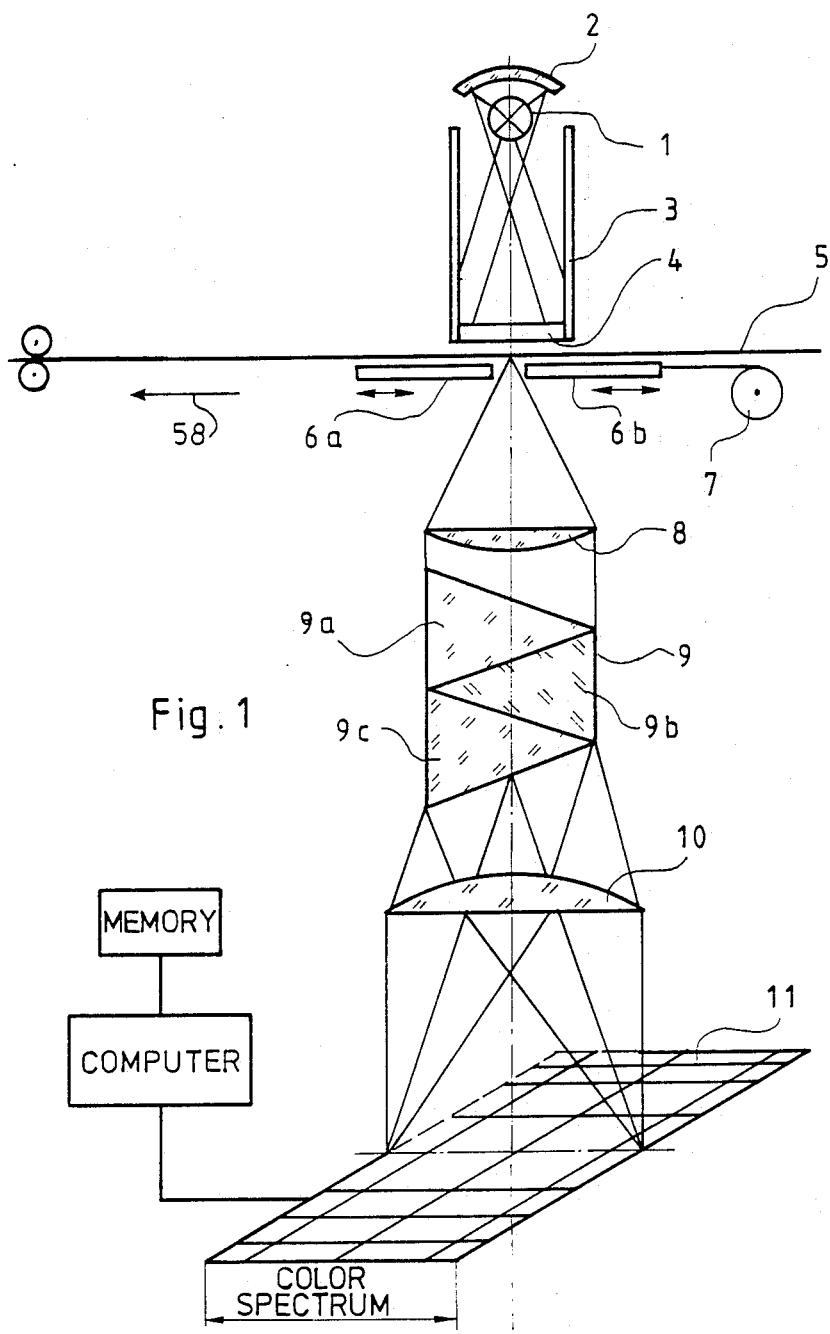
FIG. 1 schematically illustrates one embodiment of a color copying apparatus according to the invention.

FIG. 1 shows a measuring station of a color copying apparatus according to the invention. A filmstrip 5 is advanced through the measuring station along a predetermined path by suitable conveying or transporting means here shown as a pair of driven rollers 65. The filmstrip 5, which is in the form of an elongated band, carries a series of colored negatives or originals to be copied or printed in a non-illustrated copying or printing station. The rollers 65 advance the filmstrip 5 through the measuring station in the direction indicated by an arrow 58.

The measuring station is designed to measure the densities of the originals in the primary colors blue, green and red. The blue, green and red densities obtained for an original at the measuring station are used to calculate the amounts of blue, green and red copy light required to form a copy or print of the original on color copy material or paper, i.e., copy material or paper sensitized to each of the primary colors blue, green and red, in such a manner that the copy has a desired density. For instance, the amounts of copy light may be calculated so as to produce a copy of neutral gray density. In order to obtain superior results, the spectral sensitivities of the measuring station in blue, green and red are adjusted to the corresponding spectral sensitivities of the copy material.

In the illustrated embodiment, the filmstrip 5 travels through the measuring station along a horizontal path. A source 1 of measurement light, a reflector 2, a reflector shaft 3 and a scattering disc 4 are disposed immediately above this path. The source 1 emits light, e.g., white light, made up of blue, green and red radiation.

A shutter or diaphragm is located below the path of the filmstrip 5 and includes two shutter members 6a and 6b. The members 6a,6b cooperate to define a slit-like opening 6 which is elongated in a direction transverse to the path and direction of travel 58 of the filmstrip 5. The members 6a,6b are movable towards and away from one another by means of an adjusting motor 7 to permit the width of the opening 6 to be changed. The length of the opening 6 is such that the opening 6 extends entirely across an original while the width of the opening 6 is selected to be a relatively small fraction of the dimension of the original along the direction 58. Thus, only a small region of an original is exposed through the opening 6 at any instant. This allows the color densities of an original to be measured region-by-region.

The originals on the filmstrip 5 are transparent to the light emitted by the source 1. Accordingly, light from the source 1 passes through an original located at the measuring station. The light which issues from that region of the original in register with the opening 6 travels through the latter and to a collimating lens 8. The opening 6 lies in the focal plane of the lens 8. The lens 8 refracts the rays of light emanating from the opening 6 so that these become parallel to one another and directs the light to a direct-vision prism system 9. The prism system 9 is constructed in a conventional manner from a series of prisms 9a, 9b and 9c composed of different types of glass and assembled such that the central ray passes through the prism 9 with essentially no deviation in spite of spectral deflection. The light issuing from the prism system 9 travels to a focusing lens 10 which forms a sharp image of the opening 6 on a unit 11 for measuring the intensity of the light. The intensity measuring unit 11 comprises a two-dimensional or flat array of light-sensitive elements or cells which define two mutually perpendicular sets of rows. One set of rows extends in the direction of travel 58 of the filmstrip 5 while the other set of rows extends in the direction of elongation of the strip-like opening 6. The unit 11 is preferably constituted by a flat charge-coupled device.

The light which has passed through an original in the measuring station and through the opening 6 is spread out into a color spectrum by the lens system 8,10 and prism system 9 which together at least in part constitute a spectrometer. This spreading occurs along the direction of travel 58 of the filmstrip 5. The length of the spectrum, as considered along the direction 58, equals the width of the unit 11, again as considered along the direction 58, at the intersection of the spectrum and the unit 11. The blue component of the measurement light lies at the left side of the unit 11, the green component at the center and the red component at the right side.

The individual pixels or cells of the unit 11 measure the raw intensity of the measurement light. In a direction transverse to the slit-like opening 6, that is, along the direction 58, the intensity is measured at different wavelengths to generate a curve such as the curve 12 in FIG. 2a, for example. This curve, which shows raw intensity as a function of wavelength, is plotted for wavelengths between about 400 and 700 nm. A comparison of FIGS. 1 and 2a illustrates that the spectrum generated from the measurement light extends across a first wavelength range corresponding to blue-containing radiation, a second wavelength range corresponding to green-containing radiation and a third wavelength range corresponding to red-containing radiation.

For the sake of simplification, the continuous curve 12 of FIG. 2a is divided into segments each of which corresponds to a wavelength interval smaller than the first, second and third ranges. Thus, each of these ranges contains a plurality of segments. The curve 12 is here shown as being divided into segments which respectively span a wavelength interval of 20 nm although, in practice, the wavelength intervals may be much smaller than this. The raw intensities for each segment are averaged to define a point which is then plotted as illustrated in FIG. 2a. Averaging of the raw intensities may be accomplished, for example, by combining the raw intensities from several neighboring pixels or cells of a row extending along the direction 58.

The slit-like opening 6 extends across the entire width of an original as considered in a direction normal to the plane of FIG. 1 and accordingly exposes a multiplicity of scanned areas of the original along such direction. The light which passes through the original and through the opening 6 generates a color spectrum for each of these areas so that a number of spectra exist next to one another as considered normal to the direction of spread of the spectra, i.e., as considered in the direction of the slit-like opening 6. The number of spectra equals the number of scanned areas and the intensity measuring unit 11 measures the intensities of all the spectra in the same manner.

The intensity of the light source 1 in each wavelength interval to be used during copying or printing should be adequate for performance of the measuring operation. However, a spectral distribution of uniform energy is not required.

The intensity measuring unit 11 may comprise a black/white charge-coupled device. The unit 11 is then calibrated by measuring the intensities in all wavelength intervals when no film is present at the opening 6. The reference intensities obtained in this manner are stored in a memory 24. When an original is subsequently advanced to the opening 6 for measurement of the raw intensities, a ratio of the intensities with and without film is formed for each wavelength interval. Such a ratio is a measure of the transparency in the respective wavelength interval and is converted into a density by taking a logarithm. Formation of the ratios and conversion thereof into densities may be carried out by a computer 23.

As mentioned previously, the adjusting motor 7 allows the width of the opening 6, as considered along the direction 58, to be changed. This makes it possible, within certain limits determined by the required spectral precision, to adjust the size of the scanned region of an original as a function of the size of the original. Such adjustment is useful if the number of scanned regions, e.g., 30, is to remain unchanged regardless of the size of an original. By way of example, the width of the opening 6 may be reduced to such an extent for a small original that 20 to 50 regions of the original are scanned as considered along the direction 58. In contrast, no such adjustment is necessary in the longitudinal direction of the strip-like opening 6. Adjustment for the size of the original in longitudinal direction of the opening 6 is effected solely by an appropriate program for the processing of the raw intensities derived from the individual pixels of the intensity measuring unit 11. Such a program prescribes the number of pixels which are to be assigned to a scanned region.

In operation of the copying apparatus of FIG. 1, at least one color spectrum is generated for each scanned region of an original.

The curve 12 of FIG. 2a, as already indicated, represents an exemplary variation of the raw intensity within a spectrum generated from a scanned region of an original. The raw intensities of FIG. 2a are processed to yield corrected intensities which take into account the spectral sensitivities of the copy material to be used in printing the original. The copy material has respective first spectral sensitivities in each of the wavelength intervals within the wavelength range corresponding to the blue-containing portion of the spectrum; respective second spectral sensitivities in each wavelength interval within the wavelenqth range corresponding to the green-containing portion of the spectrum; and respective third spectral sensitivities in each wavelength interval within the red-containing portion of the spectrum. The first spectral sensitivities of the copy material are represented by respective first spectral sensitivity factors or first gamma values; the second spectral sensitivities by respective second spectral sensitivity factors or second gamma values; and the third spectral sensitivities by respective third spectral sensitivity factors or third gamma values.

FIG. 2b shows a table listing numbers which may be considered to constitute rough approximations for the gamma values of a conventional color copy material. The table has three rows, as well as a series of columns each of which corresponds to one of the wavelength intervals of FIG. 2a. The top row is identified as gamma$_B$ and has non-zero values only in those columns located in the first wavelength range corresponding to blue-containing radiation; the middle row is identified as gamma$_G$ and has non-zero values only in those columns located in the second wavelength range corresponding to green-containing radiation; and the bottom row is identified as gamma$_R$ and has non-zero values only in those columns located in the third wavelength range corresponding to red-containing radiation. The non-zero values in the top row represent first efficiency factors for irradiation of the copy material with blue light; the non-zero values in the middle row represent second efficiency factors for irradiation of the copy material with green light; and the non-zero values in the bottom row represent third efficiency factors for irradiation of the copy material with red light. It will be observed that the operative wavelength ranges for blue and green overlap while an inoperative wavelength interval exists around 600 nm between the wavelength ranges corresponding to green and red, i.e., the column associated with the wavelength interval of 580 to 600 nm contains only zeros.

As noted earlier, the curve 12 may be divided into wavelength intervals smaller than those illustrated in FIG. 2a. The number of columns in the table of FIG. 2b would then be increased correspondingly and the number of gamma values would likewise increase.

Multiplication of the raw intensities of FIG. 2a by the corresponding gamma values of FIG. 2b yields intensities which are corrected for, or adjusted to, the spectral sensitivities of the copy material. FIG. 2c, which is a plot of the corrected or adjusted intensities as a function of wavelength, shows that three curves 13, 14 and 15 are obtained upon multiplying the raw intensities of FIG. 2a by the associated gamma values of FIG. 2b. The curve 13 drawn with a broken line corresponds to the blue-containing portion of the spectrum and represents the effective intensities for blue radiation; the curve 14 drawn with a dotted line corresponds to the green-containing portion of the spectrum and represents the effective intensities for green radiation; and the curve 15 drawn with a dash-and-dot line corresponds to the red-containing portion of the spectrum and represents the effective intensities for red radiation. The gamma values of FIG. 2b may be considered to be weighting factors and the corrected intensities of FIG. 2c may then be considered to be weighted intensities.

The blue, green and red densities of the scanned region of the original associated with FIG. 2a are obtained by respectively summing the corrected intensities for the blue-containing portion of the spectrum, the green-containing portion of the spectrum and the red-containing portion of the spectrum. This is accomplished by integrating the areas under the curves 13, 14 and 15. The integral of the curve 13 yields a first sum representative of the blue density of the scanned region; the integral of the curve 14 yields a second sum representative of the green density of the original; and the integral of the curve 15 yields a third sum representative of the red density of the original. Depending upon the fineness of the wavelength segments and the accuracy of the gamma values, the adjustment achieved in this manner is optimal.

One or more tables, such as that of FIG. 2b, listing the gamma values for a copy material as a function of wavelength may be store in the memory 24. The gamma values may be retrieved by the computer 23 which thereupon multiplies these values by the raw intensities derived from the intensity measuring unit 11 to yield the curves 13, 14 and 15. The computer 23 may thereafter integrate the curves 13, 14 and 15 to obtain the blue, green and red densities of the respective scanned region of the original and such densities may then be stored in the memory 24.

Once scanning of an original at the measuring station has been completed, the computer 23 calculates the amounts of blue, green and red light required to print the original on the appropriate copy material such that the copy has a desired density, e.g., a neutral gray density. The calculations are performed using the blue, green and red densities which were obtained from the various scanned regions of the original and stored in the memory 24. Calculation of the required amounts of blue, green and red copy light may be carried out, for example, in accordance with the teachings of the U.S. Pat. No. 4,279,502.

Figure 3:
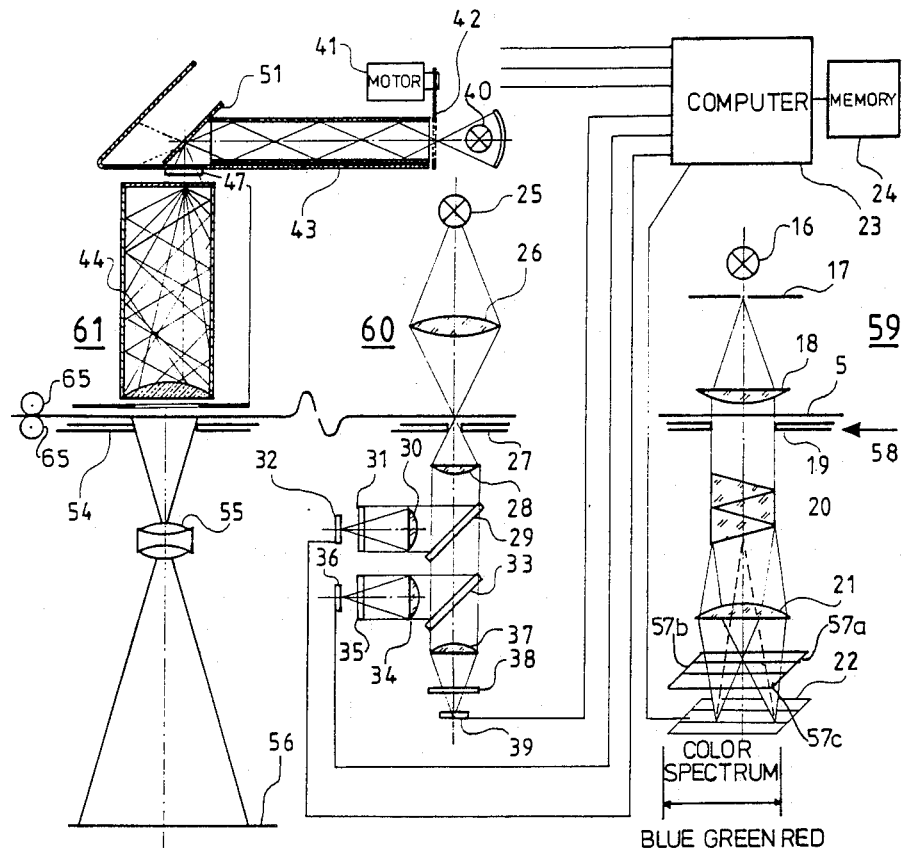
FIG. 3 schematically illustrates another embodiment of a color copying apparatus in accordance with the invention.

FIG. 3 illustrates another embodiment of a color copying apparatus according to the invention which makes it possible to reduce the amount of calculation and to achieve greater light intensities at the light-sensitive cells of a measuring station. The filmstrip 5 is again conveyed in the direction 58 and successively passes through a first measuring station 59, a second measuring station 60 and a copying or printing station 61. The first measuring station 59 once more contains a spectrometer which, however, is arrange somewhat differently than the spectrometer 8,9,10 of FIG. 1.

A source 16 of measurement light is disposed above the path of the filmstrip 5 in the measuring station 59 as is a shutter or diaphragm 17 defining an aperture. The source 16 emits light, e.g., white light, containing blue, green and red radiation. Light from the source 16 travels through the aperture in the diaphragm 17 and to a collimating lens 18 which is likewise located above the path of the filmstrip 5. The aperture of the diaphragm 17 is situated in the foal plane of the collimating lens 18. The collimating lens 18 refracts the rays of light arriving from the light source 16 so that these become parallel to one another.

A second shutter or diaphragm is disposed below the path of the filmstrip 5 and defines an opening of size equal to the major part of an original carried by the filmstrip 5 or to the entire original. The originals on the filmstrip 5 are transparent to the light emitted by the light source 16 and the parallel rays issuing from the collimating lens 18 thus successively pass through an original disposed in the first measuring station 59 and through the opening in the diaphragm 19. In contrast to FIG. 1 where the light leaving the slit-like opening 6 is light from only a small region of an original, the light leaving the opening in the diaphragm 19 is light which has passed through at least the major part of an original.

Light from the opening in the diaphragm 19 travels to a direct-vision prism system 20 similar to the direct-vision prism system 9 of FIG. 1. After passing through the prism system 20, the light arrives at a focusing lens 21 which forms a sharp image of the aperture in the diaphragm 17 on an intensity measuring unit 22. The unit 22 comprises a flat or two-dimensional array of light-sensitive elements or cells and is preferably in the form of a flat charge-coupled device.

The lens system 18,21 and prism system 20, which together at least in part constitute a spectrometer, spread out the light issuing from the aperture in the diaphragm 17 into a color spectrum. As before, the light is spread along the direction 58 such that the blue component lies at the left side of the intensity measuring unit 22, the green component at the center and the red component at the right side.

Since the light leaving the opening in the diaphragm 19 transilluminated at least the major part of an original as a whole in a structureless light path, only a single spectrum is formed at the unit 22 from the light leaving the original. As such, it would be sufficient for the unit 22 to have only a single row of light-sensitive cells. However, in order to permit better adjustment to the dynamics of the measurement light, gray filters 57a, 57b and 57c are arranged above the unit 22. The gray filters 57a,57b,57c are located next to one another as considered along a direction normal to the direction of color change of the spectrum, i.e., normal to the direction 58, and each filter 57a,57b,57c is assigned to a respective part of the spectrum, as considered normal to the direction 58, which is to be analyzed separately. The gray filters 57a,57b,57c have different densities so that the density of the filter arrangement 57a,57b,57c varies normal to the direction 58. In effect, the filters 57a,57b,57c divide the single spectrum produced from an original into three spectra of different average brightness, as considered normal to the direction of color change. The intensity measuring unit 22 has a row of light-sensitive cells corresponding to each gray filter 57a,57b,57c so that, for any original, measurements are made of the intensities of three spectra derived from the original. Each such row extends along the direction 58. The light-sensitive cells of the unit 22 have an optimum operating range and the spectrum from one of the filters 57a,57b,57c has a brightness lying in or close to this range, or at least nearer such range than the brightness of the spectrum from either of the other filters. The intensities of the spectrum having a brightness nearest the optimum operating range of the unit 22 are selected for further processing.

While three gray filters 57a,57b,57c have been shown by way of example, the number of gray filters may be different from three.

A conductor connects the intensity measuring unit 22 to the computer 23 which, as before, is coupled to the external memory 24. The memory 24 may have an opening or slot, e.g., for a floppy disc, which allows a large number of gamma values, tabulated as in FIG. 2b, for a specific color copy material to be loaded into the memory 24. A design of the memory 24 to accept floppy discs is of particular advantage when the capacity of the memory 24 is not sufficient to interchangeably store the gamma values for different copy materials. Thus, by exchanging floppy discs, it is a simple matter to rapidly adjust the copying apparatus to another copy material such as, for example, a new copy material to appear on the market.

After an original or negative leaves the first measuring station 59, the original travels in the direction 58 to the second measuring station 60. The second measuring station 60 includes a source 25 of measurement light and a condenser lens 26 both of which are disposed above the path of the filmstrip 5. The source 25 again emits light, e.g., white light, containing blue, green and red radiation.

The first measuring station 59 functions to carry out an integral spectral measurement of the blue, green and red components of a colored original.

After an original or negative leaves the first measuring station 59, the original travels in the direction 58 to the second measuring station 60. The second measuring station 60 includes a source 25 of measurement light and a condenser lens 26 both of which are disposed above the path of the filmstrip 5. The source 25 again emits light, e.g., white light, containing blue, green and red radiation.

A shutter or diaphragm 27 is located below the path of the filmstrip 5 and defines a slit-like opening which is elongated normal to the plane of FIG. 3, that is, normal to the direction 58. The condenser lens 26 directs light from the source 25 towards the slit-like opening of the diaphragm 27. The originals carried by the filmstrip 5 are transparent to the light emitted by the source 25 so that, when an original is located in the second measuring station 60, light from the source 25 passes through the original and through the opening of the diaphragm 27. The width of this opening, as considered along the direction 58, is a relatively small fraction of the length or width of an original, again as considered along the direction 58. Accordingly, the opening in the diaphragm 27 exposes a relatively small, strip-like region of an original and the light which leaves the opening is light which has passed only through such a region of the original. The slit-like opening of the diaphragm 27, which may extend entirely across an original as considered normal to the direction 58, allows the original to be scanned region-by-region.

The light emanating from the opening in the diaphragm 27 is directed to a dichroitic beam splitting unit by means of a collimating lens 28. The beam splitting unit comprises a first beam splitter 29 which reflects the blue component of the light to a focusing lens 30. The focusing lens 30 forms a sharp blue image of the slit-like opening in the diaphragm 27 on a properly positioned intensity measuring unit 32 which includes a row or an array of light-sensitive cells. By way of example, the unit 32 may be in the form of a linear charge-coupled device. A blue filter 31 of known construction is interposed between the focusing lens 30 and the unit 32 and functions to adjust the blue component of the light, as well as the spectral sensitivity of the unit 32, to the blue spectral sensitivity of the color copy material to be used in printing the original in the second measuring station 60. However, the adjustment is not perfect since the blue filter 31 is designed in a conventional manner by taking averages over different types of copy material.

The green and red components of the light issuing from the opening in the diaphragm 27 pass through the first beam splitter 29 and travel to a second dichroitic beam splitter 33. The beam splitter 33 reflects the green component of the light to a focusing lens 34 which forms a sharp green image of the opening in the diaphragm 27 on a suitably arranged intensity measuring unit 36 similar to the unit 32. A green filter 35 of known construction is located intermediate the focusing lens 34 and the unit 36 and adjusts the green component of the light and the spectral sensitivity of the unit 36 to the green spectral sensitivity of the copy material for the original. Again, the adjustment is only partial because the green filter 35 is designed conventionally by taking averages over different types of copy material.

The red component of the light emanating from the opening of the diaphragm 27 travels through the second beam splitter 33 and to a focusing lens 37 which forms a sharp red image of the opening on an appropriately positioned intensity measuring unit 39 similar to the units 31,35. A red filter 38 of known construction is interposed between the focusing lens 37 and the unit 39 and serves to adjust the red component of the light, as well as the spectral sensitivity of the unit 39, to the red spectral sensitivity of the copy material to be used for the original. As before, the adjustment is imperfect since the red filter 38 is designed in a conventional manner by averaging over different types of copy material.

The intensity measuring units 32,36,39 respectively measure the intensities of the blue, green and red components of light which has passed through a relatively small region of an original situated above the diaphragm 27. By moving an original across the opening of the diaphragm 27 in increments, the original can be scanned region-by-region to obtain blue, green and red intensities for a series of regions. The blue, green and red intensities for all scanned regions of the original are sent to the computer 23 for storage via conductors connecting the latter with the respective intensity measuring units 32,36,39.

The illustrated scanning system may be replaced by a different type of scanner on which an image of the original is formed. For example, a Nipkow disc or flat charge-coupled device suited for color may be used instead of the scanning system shown.

The computer 23 now integrates each of the blue, green and red intensities obtained from the second measuring station 60 over the area of that part of the original which was scanned in the first measuring station 59, i.e., that part of the original through which light from the source 16 travelled to the opening in the diaphragm 19. The integration for the blue intensities yields a first integral or LATD value representative of the blue density of the original; the integration for the green intensities yields a second integral or LATD value representative of the green density of the original; and the integration for the red intensities yields a third integral or LATD value representative of the red density of the original.

The computer 23 further weights the raw intensities derived from the first measuring station 59 with the respective gamma values for the copy material to be used in printing the original, i.e., the computer 23 multiplies the raw intensities by the respective gamma values. The corrected or adjusted intensities obtained in this manner are subsequently integrated by the computer 23 over a first wavelength range corresponding to blue-containing radiation, a second wavelength range corresponding to green-containing radiation and a third wavelength range corresponding to red-containing radiation. This generates first, second and third sums respectively representing the blue, green and red densities of the original. The weighting of the raw intensities and the integrations of the corrected intensities are performed as explained earlier in connection with FIGS. 2a-2c. The first, second and third sums may be considered to constitute LATD values.

The first measuring station 59 provides an optimal numerical adjustment to the spectral sensitivities of the copy material while the conventional second measuring station 60 only provides a partial or imperfect adjustment. A quotient or parameter for each of the three colors blue, green and red is now established for the original. Thus, a first quotient for the color blue is established between the first sum derived from the first measuring station 59 and the first integral value derived from the second measuring station 60; a second quotient for the color green is established between the second sum derived from the first measuring station 59 and the second integral value derived from the second measuring station 60; and a third quotient for the color red is established between the third sum derived from the first measuring station 59 and the third integral value derived from the second measuring station 60. Each of these quotients constitutes a correction factor for the respective intensities obtained at the second measuring station 60 for the scanned regions of the original, i.e., the first quotient constitutes a first correction factor for the blue intensities, the second quotient a second correction factor for the green intensities and the third quotient a third correction factor for the red intensities. As will be outlined below, these correction factors can be applied when the computer 23 sets the amount of copy light to be used in the printing or copying station 61 for each of the primary colors blue, green and red.

An original or negative enters the copying station 61 after leaving the second measuring station 60. The copying station 61 is of a conventional type having an additive lamp housing which includes three sources 40 of blue, green and red copy light, respectively. Only one of the sources 40 is visible in FIG. 3. A light beam from each of the sources 40 travels through a respective light shaft 43 to a respective dichroitic reflector 51. The reflectors 51 deflect the corresponding beams to respective color filters 47. A blue filter 47 is provided for the beam from the blue source 40; a green filter 47 for the beam from the green source 40; and a red filter 47 for the beam from the red source 40. The blue, green and red filters 47 correspond, respectively, to the blue, green and red filters 31,35,38 of the second measuring station 60. After passing through the filters 47, the beams of light arrive at a matte disc located at the entrance to a mixing shaft 44. All three light beams enter the mixing shaft 44 where they are combined and homogenized.

The amount of copy light in each primary color blue, green and red is regulated by a shutter 42 disposed in front of the respective light source 40. Each of the shutters 42 is controlled by a respective motor 41 connected to the computer 23. Illumination of an original by a light source 40 during copying can be terminated via the respective shutter 42 once the original has been exposed to the prescribed amount of light of the corresponding color.

During copying of an original, the original is located above a diaphragm 54 having an opening which frames the original. The originals carried by the filmstrip 5 are transparent to the homogenized light issuing from the mixing shaft 44 so that such light passes through an original in the copying station 61 and through the opening in the diaphragm 54. The light emanating from this opening travels to an objective 55 which forms an image of the original on color copy material 56, that is, copy material sensitized to the three primary colors blue, green and red.

In calculating the required amounts of copy light in the three primary colors, the computer 23 first calculates a raw amount of copy light for each primary color based on the blue, green and red intensities obtained at the second measuring station 60 for the different scanned regions of an original. Calculation of the raw amounts of copy light may be performed in accordance with the teachings of the U.S. Pat. No. 4,279,502 in accordance with other color correction methods based on scanning measuring systems. The correction factors for the three primary colors obtained by comparing the results of the integral measurements at the first and second measuring stations 59,60 are now applied to the end result of the intensity measurements, namely, the amounts of blue, green and red copy light calculated by the computer 23. The first correction factor is applied to the raw amount of blue copy light; the second correction factor to the raw amount of green copy light; and the third correction factor to the raw amount of red copy light. Depending upon the manner in which the correction factors are formed, the raw amounts of copy light may, for example, be multiplied by the respective correction factors.

In the method described with reference to FIG. 3, adjustment factors are thus established for each original or negative by comparing the LATD values from the precisely adjusted system 59 with the LATD values from the imperfectly adjusted system 60. These factors, when multiplied by values stored in a memory common to all films, create, so to speak, automatically, a film-specific memory which will print an original to neutral density when imperfectly adjusted measurements are employed.

The gamma values of FIG. 2b, which provide for adjustment to the particular copy material, may be derived directly from the sensitivity curves of the copy material. With reference to FIG. 1, this may be accomplished without knowledge of the spectral sensitivities of the intensity measuring unit 11 simply by performing a calibration in which the intensities with and without an original above the slit-like opening 6 are compared. There are three steps involved:

1. Determining the darkening or blackening curves in a conventional manner with a spectrum of uniform energy.
2. Modifying these curves with the spectral relative energy emissions of the printing light channels.
3. Converting these values into linear spectral values of the effective sensitivities which are normalized to 1.

A particularly simple embodiment of the method according to the invention may be achieved with a copying apparatus which is a modification of that shown in FIG. 3. In the modified apparatus, the second measuring station 60 is omitted leaving the first measuring station 59, the printing station 1, the computer 23 and the memory 24. The individual originals carried by the filmstrip 5 are scanned at the measuring station 59 to generate spectra from light which has passed through at least the major part of each original. The spectra are analyzed to yield intensities which are adjusted to the particular copy material with a high degree of precision and the intensities are processed. The resulting integrals or densities are averaged by the computer 23 and this may be accomplished, for example, in accordance with the teachings of the West German patent No. 19 14 360. In addition, the individual values are stored in order to determine, e.g., by mixing values specific to the filmstrip and values specific to the originals, the amounts of copy light which will produce neutral gray copies. The printing operations in the printing station 61 are then performed using such amounts of copy light.

The modified apparatus has the advantage that relatively few calculations are required. However, it also has the drawback that dominants resulting from color casts are not very readily recognized using the known methods such as, for instance, the method of the U.S. Pat. No. 4,406,538. This drawback is related to the fact that the measurement of light intensities for an original involves analysis of a spectrum generated by light which has passed through at least the major part of the original.

Conventional diffraction gratings can be used instead of the prism units 9,20 to spread out or separate the blue, green and red components of light which has passed through an original.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the instant contribution to the art and, therefore, such adaptations should and are intended to be comprehended within the meaning and range of equivalence of the appended claims.

What is claimed is:

1. A method of copying a colored original onto color copy material, comprising the steps of passing light through said original, said light having blue, green and red components; forming a color spectrum from the light transmitted through said original, said spectrum extending across a first wavelength range corresponding to blue-containing radiation, a second wavelength range corresponding to green-containing radiation and a third wavelength range corresponding to red-containing radiation, and said copy material having respective first, second and third spectral sensitivities in said first, second and third ranges, said first, second and third spectral sensitivities being represented by first, second and third factors, respectively; measuring the intensity of the transmitted light in said first, second and third ranges to obtain respective first, second and third raw intensities; modifying said first, second and third raw intensities by said first, second and third factors, respectively, to obtain first, second and third corrected intensities; and calculating the amounts of blue, green and red copy light which will produce a copy of said original on said copy material in such a manner that said copy has a desired density, the calculating step being performed using said corrected intensities.

2. The method of claim 1, wherein said original is a negative.

3. The method of claim 1, wherein the modifying step comprises multiplying said first, second and third raw intensities by said first, second and third factors, respectively.

4. The method of claim 1, wherein the raw intensity of the transmitted light is measured at a plurality of wavelengths in each of said ranges, each of said wavelengths lying in a respective segment of the corresponding range, and said copy material having a spectral sensitivity factor for each segment, the modifying step including modifying the raw intensity for each segment by the respective factor to obtain a corrected intensity for each segment; and further comprising the step of summing the corrected intensities for each range to obtain first, second and third sums respectively representing blue, green and red densities of said original, the calculating step being performed using said sums.

5. The method of claim 4, wherein the forming, measuring, modifying and summing steps are performed for different regions of said original individually to obtain first, second and third sums for each region, the calculating step being performed using the first, second and third sums from all of said regions.

6. The method of claim 5, further comprising the steps of conveying said original along a predetermined path, and covering all but a strip-like portion of a measuring location of said path, said strip-like portion being elongated transversely of said path.

7. The method of claim 5, further comprising the step of storing the first, second and third sums for each of said regions prior to the calculating step.

8. The method of claim 4, wherein each of the forming, measuring, modifying and summing steps is performed for at least the major part of said original at one time; and further comprising the steps of passing additional light having blue, green and red components through said part of said original, treating the transmitted additional light to partially adjust for the spectral sensitivities of said copy material, measuring the intensities of the blue, green and red components of the transmitted additional light, processing the resulting intensities to derive first, second and third values respectively representing blue, green and red densities of said original and establishing a first parameter from said first sum and said first value, a second parameter from said second sum and said second value and a third parameter from said third sum and said third value, the calculating step being carried out by calculating raw amounts of blue, green and red copy light from said first, second and third values and modifying said raw amounts of copy light by said first, second and third parameters, respectively.

9. The method of claim 8, wherein the establishing step comprises forming quotients from the respective sums and values.

10. The method of claim 8, wherein both said values and said sums represent LATD values.

11. The method of claim 4, wherein said sums represent LATD values.

12. The method of claim 11, wherein each of the forming, measuring, modifying and summing steps is performed for at least the major part of said original at one time.

13. An apparatus for copying a colored original onto color copy material, comprising means for illuminating the original with light having blue, green and red components; means for forming a color spectrum from light transmitted through the original such that the spectrum extends across a first wavelength range corresponding to blue-containing radiation, a second wavelength range corresponding to green-containing radiation and a third wavelength range corresponding to red-containing radiation, the copy material having respective first, second and third spectral sensitivities in the first, second and third ranges; means for measuring the intensity of the transmitted light in the first, second and third ranges to obtain respective first, second and third raw intensities; and means for processing the raw intensities, said processing means including storage means for first, second and third factors respectively representing the first, second and third spectral sensitivities of the copy material, and said processing means further including calculating means programmed to modify the first, second and third raw intensities by the first, second and third factors, respectively, so as to obtain first, second and third corrected intensities, said calculating means also being programmed to use the corrected intensities in calculating the amounts of blue, green and red copy light which will produce a copy of the original on the copy material in such a manner that the copy has a desired density.

14. The apparatus of claim 13, wherein said forming means comprises at least one prism and at least one lens.

15. The apparatus of claim 13, wherein said forming means comprises at least one grating and at least one lens.

16. The apparatus of claim 13, wherein said measuring means comprises a multiplicity of light-sensitive elements including a first group for the first wavelength range, a second group for the second wavelength range and a third group for the third wavelength range.

17. The apparatus of claim 13, wherein said measuring means is designed to measure the raw intensity of the transmitted light at a plurality of wavelengths in each of the wavelength ranges, each wavelength lying in a respective segment of the corresponding range, and the copy material having a spectral sensitivity factor for each segment, said calculating means being programmed to modify the raw intensity for each segment by the respective factor and to sum the resulting corrected intensities for each range to thereby obtain first, second and third sums respectively representing blue, green and red densities of the original.

18. The apparatus of claim 17, wherein said measuring means comprises a two-dimensional array of light-sensitive elements.

19. The apparatus of claim 18, wherein said measuring means comprises a charge-coupled device.

20. The apparatus of claim 18, wherein said illuminating means comprises a source of light; and further comprising a device arranged to define an elongated slit for the passage of light from said source, said slit extending in a first direction, and said elements forming first rows extending in said first direction and second rows extending in a second direction transverse to said first direction.

21. The apparatus of claim 20, wherein the width of said slit is variable.

22. The apparatus of claim 17, further comprising means for exposing the original to additional light having blue, green and red components, means for sensing the blue, green and red components of the additional light transmitted through the original to thereby determine the intensities of such components, and means for partially adjusting the spectral sensitivities of said sensing means to the spectral sensitivities of the copy material, said calculating means being programmed to process the intensities of the transmitted additional light so as to derive first, second and third values respectively representing blue, green and red densities of the original, and said calculating means additionally being programmed to establish a first parameter from the first sum and first value, a second parameter from the second sum and second value and a third parameter from the third sum and third value, said calculating means also being programmed to calculate raw amounts of blue, green and red copy light from the first, second and third values and to modify the raw amounts with the first, second and third parameters, respectively.

23. The apparatus of claim 22, wherein said adjusting means comprises filter means.

24. The apparatus of claim 22, wherein said forming means and said measuring means are arranged to receive light from at least the major part of the original at one time, said exposing means including a source of light; and further comprising a device arranged to define an opening for the passage of light from said source, said opening having a size corresponding to a minor fraction of the area of the original so as to permit the intensities of the blue, green and red components of the transmitted additional light to be determined region-by-region, said calculating means being programmed to derive first, second and third values by respectively summing the blue intensities, green intensities and red intensities for the different regions of the original.

25. The apparatus of claim 22, wherein said calculating means is programmed to establish the parameters by forming quotients of the respective sums and values.

26. The apparatus of claim 22, wherein said measuring means comprises a two-dimensional array of light-sensitive elements; and further comprising gray filter means of variable density superimposed with said array, said gray filter means being arranged such that the density thereof varies in a direction transverse to the spectrum.

27. The apparatus of claim 26, wherein said elements have an optimum operating range and said gray filter means causes selected ones of said elements to operate nearer such range than the remaining elements, said processing means being programmed to process the raw intensities from said selected elements only.

28. The apparatus of claim 22, wherein said sensing means comprises a single two-dimensional charge-coupled device.

29. The apparatus of claim 13, wherein said storage means is programmable with spectral sensitivity factors for different copy materials.

30. The apparatus of claim 29, wherein said storage means is designed to receive floppy discs.

* * * * *